United States Patent [19]
McLean

[11] Patent Number: 5,958,462
[45] Date of Patent: Sep. 28, 1999

[54] THERAPEUTIC BATH SALTS AND METHOD OF USE

[76] Inventor: Linsey McLean, 4267 S. State Rd., Davison, Mich. 48423

[21] Appl. No.: 08/862,683

[22] Filed: May 23, 1997

[51] Int. Cl.⁶ .......................... A01N 59/20; A01N 59/08; A01N 59/06; A01N 59/00
[52] U.S. Cl. .......................... 424/630; 424/663; 424/682; 424/715; 424/722; 514/886; 514/906
[58] Field of Search ..................................... 424/630, 663, 424/682, 715, 722; 514/886, 906

[56] References Cited

U.S. PATENT DOCUMENTS

| | | |
|---|---|---|
| Re. 33,512 | 1/1991 | Ramirez et al. . |
| 2,923,660 | 2/1960 | Hallmann . |
| 3,466,675 | 9/1969 | Tignor . |
| 3,853,751 | 12/1974 | Harris et al. ............................. 209/166 |
| 3,966,749 | 6/1976 | Bodor et al. . |
| 3,988,433 | 10/1976 | Benedict ................................... 424/53 |
| 4,112,066 | 9/1978 | Hussein ..................................... 424/48 |
| 4,325,962 | 4/1982 | Rainer . |
| 4,340,982 | 7/1982 | Hart et al. . |
| 4,346,709 | 8/1982 | Schmitt . |
| 4,361,587 | 11/1982 | Brule et al. . |
| 4,387,093 | 6/1983 | Lysaght . |
| 4,401,662 | 8/1983 | Lormeau et al. . |
| 4,404,105 | 9/1983 | Rysman de Lockerente et al. . |
| 4,428,958 | 1/1984 | Ponsford . |
| 4,529,721 | 7/1985 | Nagata et al. . |
| 4,582,705 | 4/1986 | Primes et al. . |
| 4,609,640 | 9/1986 | Morishita et al. . |
| 4,654,213 | 3/1987 | Ramirez et al. . |
| 4,730,052 | 3/1988 | Nakashima et al. . |
| 4,816,398 | 3/1989 | Brule et al. . |
| 4,825,025 | 4/1989 | Seaborne .......................... 219/10.55 E |
| 4,855,284 | 8/1989 | Emoedi . |
| 4,882,452 | 11/1989 | Engel et al. . |
| 4,917,891 | 4/1990 | Kaufmann et al. . |
| 5,049,389 | 9/1991 | Radhakrishnan . |
| 5,053,396 | 10/1991 | Blass . |
| 5,132,118 | 7/1992 | Mills . |

FOREIGN PATENT DOCUMENTS 275791  1/1988  Germany .

*Primary Examiner*—José G. Dees
*Assistant Examiner*—Alton Pryor
*Attorney, Agent, or Firm*—Harness, Dickey & Pierce, P.L.C.

[57] ABSTRACT

Therapeutic bath salts for the relaxation of muscles, elimination or reduction of muscle spasms, and for the overall enhancement of a person's mood. The bath salts of the present invention are used as aromatherapy that has both the convenience of a bath and the internal mechanisms of ingested medication. The formula for the composition of the present invention includes a selected amount of magnesium sulfate trihydrate (a hydrated version of epsom salts), lithium chloride, copper gluconate, and essential oils. The oils include rosewood oil, ylang ylang oil, lavender oil and patchouli oil. The oils are provided as scents for use in the prescribed aromatherapy. The user mixes a preselected amount of the crystallized salt or liquid form of the present invention with the bath water. A period of time is allowed to elapse before the user departs the bath. By resting in the tub, the user accrues the combined benefits of external therapy and internal therapy.

17 Claims, No Drawings

THERAPEUTIC BATH SALTS AND METHOD OF USE

BACKGROUND OF THE INVENTION

I. Field of the Invention

The present invention relates generally to therapeutic bath salts. More particularly, the present invention relates to a composition that includes a magnesium salt, a lithium salt, a copper salt, a carbonate, and, in its preferred form, one or more essential oils.

II. Description of the Relevant Art

Bath and bathing therapies have been known for centuries. As early as the times of ancient Egypt, wealthy families availed themselves of "scented and anointed waters" to allegedly alleviate a virtual panoply of diseases, from minor muscular discomfort to life-threatening disease.

The Romans were well known for their baths which provided both therapeutic treatment and social interaction. The ancient ruins of baths generally are found by hot springs and mineral springs, such as by the ancient city of Carcalla. The user could select from cold, warm or hot springs, and could take advantage of the high mineral content of many of these waters. Modern versions of hot springs may be found, for example, at Hot Springs, Ark.

While providing some relief for aches, pains, and disease, hot springs and mineral baths provided by nature were of only limited value to users because the therapy only had value to the extent of the temperature of the water or the minerals contained in the waters. And, of course, the user had to go to the baths, a measure which was often impractical and inconvenient.

More modern bath therapies involve the use of commercially available magnesium sulfate, or epsom salt. While this composition is available for internal as well as external use, its use in a warm bath to ease muscle pain is well known.

Unrelated to bath therapies but related to the use of magnesium sulfate are therapies that use magnesium sulfate internally for a variety of ailments. Other ingredients, however, are known for use in combination with magnesium sulfate, such as metallic elements and oils.

For example, in U.S. Pat. No. 4,582,705 issued on Apr. 15, 1986 to Primes et al., a therapeutic composition for use in detoxifying chronic alcoholics and drug addicts is disclosed. A variety of combinations of the claimed composition are set forth in that patent, and magnesium sulfate is instructed for use in several of the combinations, as is lithium and copper.

Relatedly, in U.S. Pat. No. 4,917,891 issued on Apr. 17, 1990 to Kaufmann et al. a composition having an oil emulsion is disclosed that evaporates on the wearer. While not ingested, the therapeutic use of the oil-like material apparently relies on its evaporative qualities.

An additional reference, U.S. Pat. No. 5,132,118 issued on Jul. 21, 1992 to Mills, relates to a therapeutic agent that contains, among other components, magnesium sulfate.

However, neither the historically-known baths nor the more modern compositions discloses any bath therapy that utilizes vapors as a mechanism for aromatherapy. Accordingly, the known methods for providing therapies using baths or by way of ingestion have generally failed to provide a mix of both having therapeutic advantages.

SUMMARY OF THE INVENTION

The present invention overcomes the failings of the known method of bath therapies by providing an aromatherapy that has both the convenience of a bath and the internal mechanisms of ingested medication.

More particularly, the present invention relates to therapeutic bath salts. The formula for the composition of the present invention includes selected amounts of selected ones of the following components: A magnesium salt, such as magnesium sulfate trihydrate (a hydrated version of epsom salts); a lithium salt, such as lithium chloride; a copper salt, such as copper gluconate; a carbonate (preferably sodium or potassium bicarbonate or sodium sesquicarbonate); and essential oils. Many such oils may be used, although the preferred oils include rosewood oil, eucalyptus oil, sandalwood oil, ylang ylang oil, lavender oil and patchouli oil, either alone or in various combinations. This list of preferred oils is only exemplary and is not intended as being exhaustive or limiting, as other oils may be selected. The oils are provided as scents for use in the prescribed aromatherapy.

The user mixes a preselected amount of the crystallized salt or liquid form of the present invention with the bath water. A period of time is allowed to elapse before the user departs the bath. By resting in the tub, the user accrues the combined benefits of external therapy and internal therapy.

After the allotted time, the user experiences relaxed muscles, elimination or reduction of muscle spasms, arthritic pain and swelling, and an overall enhanced feeling of well-being by alleviating depression and related moods.

The aromatherapy of the present invention provides treatment for muscular aches and pains brought about by overexertion. It also provides relief from various rheumatic disorders such as fibromyalgia.

The therapeutic salts of liquid of the present invention may be produced readily from available components for low cost.

Other advantages and features of the present invention will become apparent from the following detailed description.

DETAILED DESCRIPTION OF THE PREFERRED EMBODIMENT OF THE PRESENT INVENTION

The composition and method of use of the present invention is set forth below. However, it is envisioned that alternate compositions of the present invention may be adopted without deviating from the invention. The preferred embodiment is discussed hereafter.

The circulatory and respiratory systems of a person at rest are able to provide adequate amounts of oxygen to the muscles for aerobic respiration. This is not the case during physical exercise where muscles rely upon the anaerobic phase of respiration for energy. Anaerobic respiration causes glucose molecules to be changed to pyruvic acid. Pyruvic acid is normally introduced into the citric acid cycle to eventually lead to the synthesis of ATP. However, instead of being used in the synthesis of ATP, the reduced availability of oxygen causes pyruvic acid to be converted to lactic acid which, if ATP is available, is converted to glucose. Exercise reduces the amount of available oxygen because muscle fiber contraction relies upon ATP. The conversion of lactic acid into glucose is slowed because available ATP is being used for muscle contraction. The result is the collecting in the muscles of lactic acid. Excess acid causes deformation of protein chains because of the acid's effect on the peptide bonds of amino acids. This leads to muscle fatigue and muscle ache because the proteins, and thus the muscle fibers, now deformed, are unable to function, causing an inhibited relaxation state and a prolonged state of contraction. The addition of a base neutralizes the excess acid and causes protein chains to become substantially normal once again.

The present invention acts to counteract the effects of lactic acid at the cellular level. More particularly, by providing a warming environment, the therapeutic bath of the present invention helps to relax contractions and enhance absorption of the base minerals through tissue and cellular pores. To this end, the bath salt therapy according to the present invention has several effects.

First, chemical reactions leading to the normalization of the protein chains are normally driven by enzymes and bases. However, at times of anaerobic cellular respiration, enzymatic activity is slowed because of the lowering of both intra- and extra-cellular pH. The heating nature of the bath therapy speeds up chemical reactions in the same manner as enzymatic reactions.

Second, and related to the enzymatic engine of chemical reactions, the bath of the present invention also preferably includes copper which is known to activate and drive several anti-inflammatory enzyme systems and biochemical pathways.

Third, the deforming of the protein chains caused by excess of acid affects cellular activity as both the cellular membrane as well as the protein fractions within the cell are caused to become misshapen. The composition of the present invention provides magnesium which functions to restore the electrical potential (and thus the energy potential) of the cell across the cell membrane by balancing the calcium ions which rush into the cell upon damage to the shape or function of the cell membrane. This situation substantially results in the halting of cellular activity. The failure of cellular activity due to changes in the integrity of the cellular membrane may be likened to the wet battery which has had a barrier between adjacent cells rendered porous because of damage. Thus magnesium helps in general to restore cellular activity as well as the shape of the cell membrane and as well as restoring the shapes of the protein fragments within the cell. Magnesium also aids in the restoration of enzymatic activity.

Fourth, because the deforming of the protein chains is generally resolved by the presence of antacids, the bath of the present invention preferably includes a carbonate buffer. Preferably the carbonate buffer is sodium sesquicarbonate although sodium bicarbonate or potassium bicarbonate may also be used. Sodium sesquicarbonate is the preferred component in that it has roughly three times the buffering power of sodium bicarbonate. Potassium bicarbonate is preferred over sodium bicarbonate because it operates as a buffer without the need for sodium. In addition, sodium sesquicarbonate has cleansing properties and therefore has utility as a skin cleanser during the bath. Cleansed pores allow for improved absorption of the chemical components of the bath.

Fifth, the composition of the present invention includes lithium to help restore the user's mood. Studies have been done showing that low lithium individuals are more susceptible to either manic or unipolar depression or, possibly, to both forms of depression. Specifically, these studies reveal that there is a higher percentage of depression and higher numbers of mental institution inmates per capita in areas of the world that have low amounts of lithium in the available water supplies compared to those having higher levels of lithium.

The composition of the present invention includes as its basic components a magnesium salt, a lithium salt, a copper salt, a carbonate, and one or more essential oils.

A preferred magnesium salt is magnesium sulfate trihydrate (a hydrated version of epsom salts). According to the present invention, magnesium sulfate trihydrate (or the preferred magnesium salt) is provided in a range of between 65.0 percent and 95.0 percent by weight, although the preferred amount is approximately 79.0 percent by weight. Magnesium sulfate trihydrate appears as colorless crystals that are very soluble in water. Used in both mineral waters and as a dietary supplement, magnesium sulfate trihydrate has very low toxicity. This component of the present formula has both anti-inflammatory and anti-spasmodic characteristics.

As noted, a carbonate is used according to the compound of the present invention. While other carbonates are known the preferred one is sodium sesquicarbonate. As used in the present invention, sodium sesquicarbonate is preferably provided in a range of between 5.0 percent and 35.0 percent by weight, although the preferred amount is approximately 20.0 percent by weight. Sodium sesquicarbonate appears as white, needle-shaped crystals that are soluble in water. As a mild alkaline agent, sodium sesquicarbonate is present in the present invention for its general cleaning and water softening properties.

As noted, the preferred lithium salt is lithium chloride. Lithium chloride as used in the present invention is provided in a range of between 0.1 percent and 5.0 percent by weight, although the preferred amount is approximately 1.0 percent by weight. Also in crystallized form at room temperature, lithium chloride crystals have a white appearance. The crystals are highly soluble in water and, because they are deliquescent, it is the lithium chloride component of the therapeutic bath salts of the present invention that requires the composition to be closely stoppered or otherwise enclosed when stored. Lithium chloride itself has low toxicity, but its use as a dietary salt substitute by direct ingestion is discouraged. This component finds particular application here to raise the person's mood and to thereby reduce depression.

Also as noted, the preferred copper salt is copper gluconate. Copper gluconate as used in the present invention is provided in a range of between 0.001 percent and 4.0 percent by weight, although the preferred amount is approximately 1.0 percent by weight. Generally used as a dietary supplement, copper gluconate is an odorless, fine, light blue crystalline powder that is soluble in water. As used in the composition of the present invention, copper ions temporarily relieves arthritis inflammation and swelling. It should be noted that the gluconate form of copper is preferred over most other copper salts as the others tend to be acidic and irritating to the skin. Copper gluconate is a mildly stable organic chelate and other chemical forms of copper that also show these same or similar properties may be substituted as price and availability become competitive.

The essential oils (so called because they contain the "essence"—odor or flavor—of the parent plant) as used in the present invention are provided in a range of between 1.0 and 5.0 cc's per dose. Commonly used in perfumery and as flavors because of their odoriferous properties, essential oils are volatile liquids that are both naturally and synthetically derived. Essential oils are generally insoluble in water, although the individual constituents of some oils are partially water soluble. Although there are a variety of essential oils including, for example, oil of wintergreen, oil of cloves, oil of nutmeg, oil of aniseed, oil of vanilla bean, oil of thyme and mint, oil of sassafras, rose oil, orange oil, and oil of rosemary, the preferred essential oils of the present invention include rosewood oil, ylang ylang oil, lavender oil, and patchouli oil.

A single bulk production of the composition included approximately 20 pounds of magnesium sulfate trihydrate, 5 pounds sodium sesquicarbonate, ¼ pound lithium chloride, and ⅛ pound copper gluconate. This composition yielded 57 individual whole-body baths. Between 1 and 5 cc's of one or more of the essential oils was also included per dose in combination with the powder base.

In particular, ylang ylang oil is a yellowish, volatile oil distilled from the flowers of Cananga odorata and finds common use in perfumes. Lavender oil is also used commonly in perfumes. Patchouli oil is a yellowish-to-brownish oil used in both perfumes and flavoring.

The essential oils of the present invention have application as scents.

In use, a selected amount of the composition (preferably between two and eight ounces) of the present invention is dissolved in hot bath water. The bather can either use the treated water locally, for example, in a bowl in which a hand or foot is soaked, or may be used in a body-immersing bath in which case between two to eight ounces per tub-full is recommended. The user then soaks himself in the water for a comfortable period of time, for example, between thirty and ninety minutes, or until the bath water begins to cool. Because there is no direct ingestion of the composition of the present invention and because, in any event, the principal ingredients of the present invention have low toxicity, the therapy may be repeated on an "as needed" basis as often as required.

The hot or warm bath water opens the user's pores thus allowing the salts of the composition to enter the user through the skin. The diluted salts of the present invention create an ionic osmotic high-to-low concentration, thus enabling the salts to enter the skin with relative ease. Accordingly, the dosage of the solution of the present invention is variable depending on whether the water is "hard" or "soft".

Once used as prescribed, the aromatherapy of the present invention relaxes muscles, eliminates or reduces muscle spasms, temporarily alleviates the pain and inflammation of arthritis and fibromyalgia, and enhances overall feelings of well-being.

The invention will be better understood from a consideration of the following examples. All percentages are based upon weight.

EXAMPLE

Therapeutic Bath Salts and Method of Use

As discussed, the present invention includes selected amounts of magnesium sulfate trihydrate, lithium chloride, copper gluconate and particular essential oils. According to the present example, the composition was established by the commingling of 78.8 percent magnesium sulfate trihydrate, 19.7 percent sodium sesquicarbonate, 1.0 percent lithium chloride, 0.5 percent copper gluconate, and 3.0 cc's rosewood oil. The user, suffering from muscle cramps derived from over exertion, poured approximately four ounces of the composition into a tub-full of hot water. The user remained almost entirely immersed in the water for a period of 50 minutes. The user's muscle cramping was relieved and an overall improvement of the user's spirits was noted.

The invention being thus described, it will be obvious that the same may be varied in many ways. Such variations are not to be regarded as a departure from the spirit and scope of the invention, and all such modifications are intended to be included within the scope of the following claims.

What is claimed is:

1. A composition of matter for use relaxation, inflammation, and pain therapy which comprises:

between 65.0 and 95.0 percent by weight a magnesium compound;

between 5.0 and 35.0 percent by weight a carbonate compound; and between 0.001 percent and 4.0 percent by weight a copper compound.

2. The composition of matter of claim 1, further including a selected amount of an essential oil, said essential oil being one or more oils selected from the group consisting of rosewood oil, eucalyptus oil, ylang ylang oil, lavender oil, and patchouli oil.

3. The composition of matter of claim 1 wherein said carbonate compound is sodium sesquicarbonate.

4. The composition of matter of claim 1, wherein said carbonate compound is sodium bicarbonate.

5. The composition of matter of claim 1, wherein said lithium compound is lithium chloride.

6. The composition of matter of claim 1, wherein said magnesium compound is magnesium sulfate.

7. The composition of matter of claim 6, wherein said magnesium sulfate is magnesium sulfate trihydrate.

8. The composition of matter of claim 1, wherein said composition is administered in doses, a dose of said composition being between 2 ounces and 8 ounces.

9. The composition of matter of claim 8, wherein said essential oil is provided in the amount of between 1.0 cc and 5.0 cc's per dose.

10. A process for preparing a composition of matter for use in aromatherapy, the process including the steps of:

commingling between 65.0 percent and 95.0 percent by weight a magnesium salt, between 5.0 percent and 35.0 percent by weight a carbonate compound to create a first part; and adding between 0.001 percent and 4.0 percent by weight a copper salt to said first part to create a second part.

11. The process of claim 10, wherein said magnesium salt is magnesium sulfate.

12. The process of claim 11, wherein said magnesium sulfate is magnesium sulfate trihydrate.

13. The process of claim 10, wherein said carbonate compound is sodium bicarbonate.

14. The process of claim 10, wherein said carbonate compound is sodium sesquicarbonate.

15. The process of claim 10, wherein said carbonate compound is potassium bicarbonate.

16. The process of claim 10, further including the step of adding between 0.1 percent and 5.0 percent by weight a chloride salt to said first part, wherein said chloride salt is lithium chloride.

17. The process of claim 10, further including the step of adding an essential oil to said second part, wherein said essential oil is one or more oil selected from the group consisting of oil of wintergreen, oil of clove, oil of nutmeg, oil of anise, oil of vanilla, oil of thyme, oil of mint, oil of sassafras, oil of rose, oil of orange, rosewood oil, eucalyptus oil, ylang ylang oil, lavender oil, and patchouli oil.

* * * * *

UNITED STATES PATENT AND TRADEMARK OFFICE
CERTIFICATE OF CORRECTION

PATENT NO. : 5,958,462
DATED : September 28, 1999
INVENTOR(S) : Linsey McLean

It is certified that error appears in the above-identified patent and that said Letters Patent is hereby corrected as shown below:

Column 1, line 53, "use" should be --value--.

Column 1, line 53, after "material" please insert --is--.

Column 1, line 54, "relies" should be --founded--.

Column 3, line 38, "as well as restoring" should be --restores--.

Column 3, line 59, after "both" please insert --.-- and please delete "forms of depression".

Column 4, line 46, "relieves" should be --relieve--.

Column 4, line 50, "chelate and other" should be "chelate. Other--.

Column 6, line 5, claim 1, after "use" please insert --in--.

UNITED STATES PATENT AND TRADEMARK OFFICE
CERTIFICATE OF CORRECTION

PATENT NO. : 5,958,462
DATED : September 28, 1999
INVENTOR(S) : Linsey McLean

It is certified that error appears in the above-identified patent and that said Letters Patent is hereby corrected as shown below:

Column 6, line 22, claim 5, the claim should read --The composition of matter of Claim 1, further including between 0.1 percent and 5.0 percent by weight of a chloride salt wherein said chloride is lithium chloride.--.

Column 6, line 58, claim 17, both occurrences of "oil" should be --oils--.

Signed and Sealed this

Tenth Day of April, 2001

Attest:

NICHOLAS P. GODICI

Attesting Officer

Acting Director of the United States Patent and Trademark Office